United States Patent [19]

Olson

[11] Patent Number: 5,085,987

[45] Date of Patent: * Feb. 4, 1992

[54] IMMUNOSEPARATING STRIP

[75] Inventor: John D. Olson, Sunnyvale, Calif.

[73] Assignee: Syntex (U.S.A.) Inc., Palo Alto, Calif.

[*] Notice: The portion of the term of this patent subsequent to Apr. 26, 2005 has been disclaimed.

[21] Appl. No.: 566,949

[22] Filed: Aug. 13, 1990

Related U.S. Application Data

[63] Continuation of Ser. No. 13,615, Feb. 12, 1987, Pat. No. 4,963,468, which is a continuation-in-part of Ser. No. 904,597, Sep. 5, 1986, Pat. No. 4,959,307.

[51] Int. Cl.$^5$ ............... G01N 33/538; G01N 33/543; G01N 33/548
[52] U.S. Cl. ..................... 435/7.91; 422/56; 435/7.93; 435/970.975; 436/501; 436/514; 436/518; 436/530; 436/541; 436/810; 436/815; 436/816
[58] Field of Search ............... 435/7, 805, 810, 7.93, 435/970, 975, 7.91; 422/56; 436/501, 514, 518, 530, 810, 815, 816, 541

[56] References Cited

U.S. PATENT DOCUMENTS

| | | | |
|---|---|---|---|
| 4,740,468 | 4/1988 | Weng et al. | 435/7 |
| 4,806,311 | 2/1989 | Greenquist | 435/7 |
| 4,861,711 | 8/1989 | Freisen et al. | 435/805 |

FOREIGN PATENT DOCUMENTS 0191640  8/1986  European Pat. Off. .

Primary Examiner—David Saunders
Attorney, Agent, or Firm—Theodore J. Leitereg

[57] ABSTRACT

A method and device for determining the presence of an analyte in a sample suspected of containing the analyte is disclosed. The method involves contacting a test solution containing the sample, an antibody for the analyte, and a conjugate of the analyte and a label with a contact portion of a piece of bibulous material capable of being traversed in at least one direction by the test solution through capillary action. The bibulous material contains a first receptor capable of binding to said conjugate. The first receptor is non-diffusively bound to a situs on the bibulous material separate from the contact portion. The bibulous material further contains a second receptor capable of binding the antibody to the analyte between the situs and the contact portion. The second receptor is non-diffusively bound to the bibulous material. At least a portion of the test solution is allowed to traverse the bibulous material by capillary action and thereby contact the situs. The situs is examined for the presence of the conjugate. To this end, the situs can be exposed to a signal producing means capable of interacting with the label to produce a signal in relation to the amount of analyte in the test solution. The signal produced at the situs is then detected.

15 Claims, No Drawings

IMMUNOSEPARATING STRIP

This is a continuation of pending application Ser. No. 07/013,615, filed Feb. 12, 1987, now U.S. Pat. No. 4,963,468, which in turn is a continuation-in-part of pending application Ser. No. 06/904,597, filed Sept. 5, 1986, now U.S. Pat. No. 4,959,307, the disclosures of which are incorporated herein by reference.

BACKGROUND OF THE INVENTION

1. Field of the Invention

The ability to employ naturally occurring receptors or antibodies directed to specific compounds in assaying for the presence of a compound of interest has created a burgeoning immunoassay business. In each of the assays, a homologous pair of specific binding pair ("sbp") members, usually an immunological pair, involving a ligand and a receptor (antiligand) is involved, wherein one of the sbp members is labeled with a label which provides a detectible signal. The immunoassay methodology results in a distribution of the signal label between signal label bound in a complex of the sbp members and unbound signal label. The differentiation between bound and unbound signal label can be as a result of physical separation of bound from unbound signal label or modulation of the detectible signal between bound and unbound signal label.

For the most part, immunoassays have been directed to quantitative determination of a wide variety of compounds of interest in clinical laboratories requiring relatively sophisticated equipment and careful technique. Immunoassays have found less extensive commercial application where semi-quantitative or qualitative results would be acceptable and the determination would involve non-laboratory personnel, such as in a home or a medical practitioner's office. Even in the clinical laboratory, simple and rapid screening tests employing inexperienced personnel could serve to provide substantial economies.

In developing an immunoassay, there are many considerations. One consideration is to provide substantial differentiation between the observed signal resulting from signal label when bound as compared to unbound. Another consideration is to minimize interference from endogenous materials in the sample suspected of containing the compound of interest. A further consideration is the ease with which the observed signal can be detected and serve to differentiate between concentrations in the concentration range of interest. Other factors include the ease of preparation of the reagents, the accuracy with which samples and reagent solutions must be prepared and measured, the storage stability of the reagents, the number of steps required in the protocol, and the proficiency and accuracy with which each of the steps must be performed. Therefore, in developing an assay which can have application with untrained personnel, such as assays to be performed in the home, in forensic medicine, by medical practitioners, or the like, the observed result should be minimally affected by variations in the manner in which the protocol is carried out or provide for simple techniques for performing the various steps.

2. Description of the Prior Art

A test device for determining a characteristic of a sample, particularly for determining substances in fluid samples, is disclosed in U.S. Pat. No. 4,094,647. A thin layer chromatography device and method of making a chromatography test is disclosed in U.S. Pat. No. 4,384,958. An immunoassay wherein labeled antibody is displaced from immobilized analyte analog is described in U.S. Pat. No. 4,434,236. A device and method for detecting myoglobin is disclosed in U.S. Pat. No. 4,189,304. Test strips for analyzing substances dissolved in liquids are described in U.S. Pat. No. 4,438,067. A multi-layered test device for determining the presence of a liquid sample component and the method of using such a device, are described in U.S. Pat. No. 4,160,008. A method for measuring antigen by labeled antigen using insoluble antibody is disclosed in Japanese Patent Application Laid—Open No. 5925/73—Jan. 25, 1973.

A concentrating zone method in heterogeneous immunoassays is disclosed in U.S. Pat. No. 4,366,241. U.S. Pat. No. 4,168,146 describes an immunoassay test strip. U.S. Pat. Nos. 3,990,850 and 4,055,394 describe diagnostic test cards. An automated method for quantitative analysis of biological fluids is described in U.S. Pat. No. 4,327,073. A chromogenic support immunoassay is disclosed in International Application No. PCT/US83/01887.

A wide variety of patents and patent applications provide an extensive literature of different techniques for producing detectible signals in immunoassays. The following list is merely illustrative of some of these techniques which can find application in this invention. The following is a list of United States patents and patent applications and a general statement of the type of label involved:

U.S. Pat. Nos. 3,646,346, Radioactive Label; 3,654,090, 3,791,932 and 3,817,838, Enzyme Labels; 3,996,345, Fluorescer-Quencher Labels; 4,062,733, Radioactive Label; 4,067,959, Fluorescer or Enzyme Label; 4,104,029, Chemiluminescent Label; and 4,160,645, Non-Enzymatic Catalyst Label. See U.S. Pat. Nos. 3,966,879 for an electrophoretic technique employing an antibody zone and 4,120,945 for an RIA where labeled analyte is initially bound to a solid support through antibody. U.S. Pat. No. 4,233,402 employs enzyme pair labels; U.S. Pat. No. 4,720,450, chemically induced fluorescent labels; and U.S. Pat. No. 4,287,300, enzyme anionic charge labels.

SUMMARY OF THE INVENTION

The methods and devices of the present invention are useful for determing the presence of an analyte in a sample suspected of containing the analyte. The device is a piece of bibulous material capable of being traversed in at least one direction by a test solution through capillary migration. The test solution is comprised of the sample, an antibody for the analyte, and a conjugate of the analyte and a label. The bibulous material contains a first receptor for the conjugate non-diffusively bound to a situs on the bibulous material separated from a contact portion. The contact portion of the bibulous material provides for contacting with the test solution. The bibulous material further contains a second receptor capable of binding the antibody for the analyte. The second receptor is non-diffusively bound to the bibulous material at least between the situs and the contact portion.

In the method a contact portion of the bibulous material separated from the situs is contacted with the above test solution, which traverses the bibulous material in at least one direction by means of capillary action. At least a portion of the test solution is allowed to traverse the bibulous material. The situs is then examined for the presence of conjugate. For example, the situs can be exposed to a signal producing means capable of interacting with the label to produce a signal in relation to the amount of analyte in the test solution. The signal is detected at the situs. Alternatively, the situs can be examined directly for the presence of a signal where a label such as a radioactive material is employed.

In one embodiment of the present invention the signal produced at the small situs has a sharp-edged distinctive pattern that provides a sharp contrast to the signal produced at portions of the bibulous material other than at the situs when analyte is present in the test solution.

In another embodiment of the present invention, the first receptor is non-diffusively bound to a small situs on the bibulous material through the intermediacy of particles non-diffusively bound to the small situs.

The method and device of the present invention are advantageous because the device is a standard reagent that can be applied to a plurality of analytes in a single test solution or multiple test solutions. The presence or absence of one or more analytes in the test solution can be readily determined using a single piece of bibulous material and appropriate antibodies and conjugates. In addition, the method of the invention provides for the detection of analytes, such as drugs, without the need for reference materials or instrumentation. The present method and device allow for simple and efficient separation of conjugate bound to antibody and unbound conjugate. No wash step is necessary although a wash step can be included. In addition, the analyte is conjugated to a label and one can achieve very high levels of labeling up to 100%. This is particularly important where the label is an enzyme. The enzyme activity is retained at a high level and the conjugate is very immunoreactive. The prior art methods often employ a labeled antibody. In such a case 100% labeling is not achieved with enzyme having a high level of activity.

DESCRIPTION OF THE SPECIFIC EMBODIMENTS

As mentioned above, the present invention is directed to methods and devices for determining the presence of an analyte in a sample suspected of containing the analyte. A test solution is formed by combining in an aqueous medium the sample, an antibody for the analyte, and a conjugate of the analyte and a label. A portion, i.e., the "contact portion", of a piece, e.g., strip, of bibulous material capable of being traversed in at least one direction by this test solution by means of capillary migration is contacted with the test solution. The bibulous material contains a first receptor capable of binding to the conjugate. The first receptor is non-diffusively bound to a situs on the bibulous material. The bibulous material further contains a second receptor capable of binding the antibody to the analyte. The second receptor is non-diffusively, and preferably uniformly, bound to the bibulous material at least at a portion thereof between the situs and the contact portion. At least a portion of the test solution is allowed to traverse the bibulous material by capillary action and thereby contact the situs. Next, the situs is examined for the presence of conjugate. In one embodiment the situs is exposed to a signal producing means capable of interacting with the label to produce a signal in relation to the amount of analyte in the test solution. The signal produced at the situs is then detected. In another embodiment signal at the situs is directly detected.

The second receptor provides a means for seperating conjugate bound to the antibody ("bound conjugate") from conjugate not bound to antibody ("unbound conjugate"). The first receptor binds unbound conjugate and the label, which either directly or in conjunction with the signal producing means provides a detectible signal at the situs in relation to the amount of analyte in the sample. The surface area of the situs is less than that of the piece of bibulous material.

The signal producing means is reactive with the label and includes reagents required to produce a detectible signal at the situs in relation to the presence or amount of analyte in the sample.

In one embodiment of the present invention the first receptor is conjugated to particles, which particles are non-diffusively bound to the bibulous material at the situs. The situs can be a narrow or wide band running transverse to the direction of traversal of the test solution along the bibulous material. The signal produced at the situs can be a narrow or wide band, a sharp-edged distinctive pattern, or the like. The signal generated at the situs can be compared with adjacent areas on the bibulous material. On the other hand, in, for example, some quantitative assays the signal can be measured directly at the situs without comparison with adjacent areas on the bibulous material.

The present invention can be applied to the determination of the presence of a plurality of analytes in a test solution.

Before proceeding further with the description of the specific embodiments of the present invention, a number of terms will be defined.

Analyte—the compound or composition to be measured that is capable of binding specifically to an antibody, usually an antigen or drug.

The precise nature of the antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The analytes are characterized by having single binding sites (monovalent) or multiple binding sites (polyvalent). The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes and the like.

The monovalent analytes will generally be from about 100 to 2,000 molecular weight, more usually from about 125 to 1,000 molecular weight. The analytes of interest include drugs, hormones, metabolites, pesticides, pollutants, and the like.

Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular or ring members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g., $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

"Antibody"—an immunoglobulin or derivative or fragment thereof having an area on the surface or in a cavity which specifically binds to and is thereby defined as complementary with a particular spatial and polar organization of another molecule. The antibody can be monoclonal or polyclonal and can be prepared by techniques that are well known in the art such as immunization of a host and collection of sera or hybrid cell line technology.

"Antibody for the analyte"—an antibody specific for an analyte.

"Receptor"—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, avidin, protein A, complement component Clq, and the like.

"First receptor"—a receptor capable of binding to a conjugate of an analyte and a label. The receptor can bind to a determinant site on the analyte or label portion of the conjugate or to a determinant site that involves both the analyte and the label. A preferred first receptor is an antibody and, more preferably, an antibody for the label portion of the conjugate.

"Second Receptor"—a receptor capable of binding an antibody for the analyte. A preferred second receptor is an antibody capable of binding to the antibody for the analyte. The second receptor antibody can be raised in a different species than that used to raise the antibody for the analyte. For example, if the antibody for the analyte is from a murine source, a goat can be immunized with the murine antibody to yield the second receptor antibody. In another embodiment antibody for analyte can be conjugated to a hapten such as biotin and the second receptor can be specific for such hapten such as, e.g., antibiotin or avidin.

"Analyte analog"—a modified analyte or analyte analog surrogate which can compete with the analogous analyte for a receptor or antibody, the modification providing means to join an analyte analog to another molecule. The analyte analog will usually differ from the analyte by more than replacement of a hydrogen with a bond which links the analyte analog to a hub or label, but need not. The term analyte surrogate refers to a compound having the capability of binding the antibody for the analyte. Thus, the analyte surrogate may bind to the antibody for the analyte in a manner similar to the analyte. On the other hand, the surrogate could be, for example, an antibody directed against the idiotype of an antibody to the analyte.

Bibulous material—a porous material having pores of at least $0.1\mu$, preferably at least $1.0\mu$, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized to permit covalent bonding of receptors or antibodies as well as to permit bonding of other compounds which form a part of the signal producing system.

Binding of receptors and antibodies to the bibulous material may be accomplished by well-known techniques, commonly available in the literature. See, for example, "Immobilized Enzymes," Ichiro Chibata, Halsted Press, New York (1978) and Cuatrecasas, *J. Bio. Chem.*, 245:3059 (1970).

The piece of bibulous material can be a single structure such as a sheet cut into strips or it can be several strips or particulate material bound to a support or solid surface such as found, for example, in thin-layer chromatography and can have an absorbent pad either as an integral part or in liquid contact therewith. The absorbent pad may be any hydrophilic bibulous material such as paper, sponge, felt, porous polymers and the like. The piece of bibulous material can be comprised of segments, such as pads, bound to a support. The piece of bibulous material can be a sheet having lanes thereon, or be capable of spotting to induce lane formation, wherein a separate assay can be performed in each lane. The piece of bibulous material can have a shape that is rectangular, circular, oval, triagonal, or the like, provided that there is at least one direction of traversal of a test solution by capillary migration. Other directions of traversal may occur such as in an oval or circular piece contacted in the center with the test solution. However, the main consideration is that there be one direction of flow to a situs. In the following discussion strips of a bibulous material will be described by way of illustration and not limitation.

The support for the bibulous material where a support is desired or necessary will normally be water insoluble, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the strip, or non-specifically bind assay components, or interfere with the signal producing system. Illustrative polymers include polyethylene, polypropylene, poly(4-methylbutene), polystyrene, polymethacrylate, poly(ethylene terephthalate), nylon poly(vinyl butyrate), glass, ceramics, metals, and the like.

"Conjugate"—a conjugate comprising—a label, for example, a catalyst, usually an enzyme, conjugated to an analyte.

"Label"—A label may be any molecule bound or conjugated to the analyte that is required to produce a signal. In the subject invention, the label can be inert and serve solely as a binding site for a member of the signal producing means or it may spontaneously produce a detectible signal or it may produce a detectible signal in conjunction with a signal producing means. The label may be isotopic or nonisotopic, preferably nonisotopic. However, an isotopic label can be preferred for achieving high sensitivity when using radioautographic detections with photographic film.

"Signal producing means"—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to the strip.

"Signal Producing System"—The signal producing system may have one or more components, at least one component being the conjugate of the analyte and a label. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal-producing system can include at least one catalyst as a label, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal at the situs, related to the amount of lablel bound to the situs, as a result of the binding of the conjugate to the situs by means of the first receptor.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the compound that produces a signal to provide the compounds that generates the signal.

Where enzymes are employed, the involved reactions will be, for the most part, hydrolysis or redox reactions. In the case of hydrolysis, a derivatized dye precursor that has an enzymatically labile bond and an enzyme that catalyzes its conversion to an insoluble dye product, is illustrative of this type of system. In redox reactions, a first enzyme would produce an essential oxidizing substrate required for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosophate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued July 10, 1979, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the bibulous material, while the other enzyme is the label conjugated to the analyte. Additionally, one or more other members of the signal producing system can be bound to the bibulous material depending on the particular signal producing system chosen or the particular protocol followed.

In order to have a detectable signal, it is desirable to provide means for amplifying the signal produced by the presence of the label bound at the situs. Therefore, it will usually be preferable for the label to be a catalyst or luminescent compound or radioisotope, most preferably a catalyst. Preferably, catalysts are enzymes and coenzymes which can produce a muliplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and $\beta$-galactosidase. Alternatively luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

"Ancillary Materials"—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly non-ionic surfactants, binding enhances, e.g., polyalkylene glycols, or the like.

"Situs"—an area on the piece of bibulous material which has a surface area less than the surface area of the piece of bibulous material. The situs may be a narrow or wide line, curve, or band, a dot, a pattern formed from dots, lines, curves, bands, or combinations thereof, or the like.. Generally, the direction of traversal of the bibulous material by the test solution will be transverse to the situs. In one embodiment the situs is a wide band removed from the contact end of the strip. In another embodiment the signal produced at the situs has a sharp-edged distinctive pattern that provides a sharp contrast to signal produced at portions of the strip other than the situs. For example, the situs can be a printed display of an abbreviated name or names of the analyte or analytes in the test solution, of a plus sign, or the like. The situs is separated from the portion of the bibulous material ("contact portion") contacted with the test solution in accordance with the separating principle of the present invention. The portion of the bibulous material between the situs and the contact portion should be large enough to provide sufficient separation of bound and unbound conjugate prior to the test solution reaching the situs.

In the method of the invention, an antibody for the analyte and a conjugate of the analyte and a label are combined in an aqueous medium with a sample suspected of containing the analyte to provide an aqueous test solution. Alternatively, the conjugate of the analyte and a label and the antibody for the analyte can be combined first and the combination subsequently combined with the sample or the combination of one or more of the above can take place on the bibulous material. The primary consideration is that a test solution containing the sample come in contact with the antibody for the analyte and a conjugate of the analyte and a label prior to or at the contact portion of the bibulous material. A first receptor capable of binding to the conjugate is non-diffusively bound to the bibulous material at the situs. The second receptor is non-diffusively bound to the bibulous material between the situs and the contact portion. The contact portion of the bibulous material is contacted with the test solution, which will traverse the bibulous material through capillary action. This transversal can be upward, downward, horizontal or combinations thereof. The amount of the conjugate that becomes bound to the situs throug binding to the first receptor is related to the amount of analyte in the sample. The signal producing system provides a detectible signal at the situs only when the conjugate is bound, so that the presence of the analyte may be determined by detecting the signal at the situs. Binding of the conjugate and the first receptor may occur directly to a binding site on the label or the analyte. Binding may also occur at a site characteristic of the conjugate of the analyte and the label which site is not present in either component alone.

The present invention provides for an immunoseparation of bound conjugate from unbound conjugate. This is accomplished by having the second receptor non-diffusively bound to the bibulous material at least between the situs and the contact portion. A second receptor will normally be chosen that provides for direct binding to the antibody for the analyte. Generally, the amount of second receptor bound to the bibulous material should be sufficient to bind all of the antibody for the analyte present in the test solution. Usually, the second receptor will be present in an excess amount.

The movement of the test solution along the bibulous material is due to capillarity. This capillary movement along the bibulous material causes the test solution to be carried to and through the situs.

After the bibulous material has been contacted with the test solution, the bibulous material is exposed to the signal producing means. Depending on the label and the signal producing means, such exposure may be the result of irradiation, heating, or contact with chemical agents. In the latter instance a developer solution containing the chemical agents can be contacted with the situs. The situs can be immersed in the developer solution after the contact portion of the bibulous material has been contacted with the test solution which subsequently passes through the situs. In another approach, the developer solution can be contacted with the contact portion of the bibulous material and allowed to move to the situs by capillary action.

The solvent for the test solution and/or the developer solution will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent. Under some circumstances depending on the nature of the sample, some or all of the aqueous medium could be provided by the sample itself.

The pH for the medium will usually be in the range of 4–11, usually 5–10, and preferably in the range of about 6–9. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Desirably, from about 0.05 to 0.5 wt. % of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the assay and production of a detectable signal will generally be in the range of about 4°–50° C., more usually in the range of about 10°–40° C., and frequently will be ambient temperatures, that is, about 15°–25° C.

The concentration, in the liquid sample, of analyte which may be assayed will generally vary from about $10^{-4}$ to about $10^{-15}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

The size of the piece of bibulous material is dependent on several considerations. The primary consideration is to separate unbound conjugate from bound conjugate and to capture a sufficient amount of unbound conjugate at the situs to give a sufficient signal so that a sensitive and accurate assay is achieved. The following discussion is primarily focused on strips of bibulous material for purpose of illustration and not limitation. As mentioned above, other shapes such as circular, oval, triagonal, and the like, fall equally within the scope of this invention. The dimensions thereof and other parameters can be determined by those skilled in the art with reference to the disclosure herein.

When capillary flow is predominantly upward, the length and thickness of the strip control the amount of solution that can pass through the situs. If the transfer of a large volume of test solution is desired, the fluid capacity of the strip above the situs must be sufficient to accomodate the desired volume. If the strip is used to provide a predominantly downward flow so as to syphon the test solution this volume requirement is not needed. Moreover, if an absorbant material is provided to contact the end of the strip not used to contact the test solution the volume requirement is also eliminated. In general, for upward flow strips the fluid retention volume between the situs and the contact portion will be usually greater than 20 $\mu$L, preferably at least 50–200 $\mu$L. For downward flow strips retention volumes as low as 2–20 $\mu$L can be used but volumes of 20–200 $\mu$L are preferable.

Thickness of the strips will usually be no greater than 20% of the width, preferably 1 to 10%, more preferably 2 to 5%.

To permit conservation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The length of the strip will depend on the concentration of the analtye and practical considerations such as ease of handling and the number of situses on the strip and will be about 2 cm to 40 cm, usually about 4 cm to 25 cm, preferably about 6 to 20 cm but may be of any practical length. The structure of the strip can be varied widely and includes fine, medium fine, medium, medium coarse and coarse. In general, smaller pore size and finer material will provide slow capillary flow and efficient capture of bound conjugate on the strip. Courser, more porous materials provide faster flow, but the efficiency of capture is reduced. Selection of the porosity of the material depends on the rate of binding of the components for a given assay.

The position of the situs, or situses, where a plurality of analytes are being determined, should be governed by the basic principle involved in the present invention. One desires to pass by capillarity a sufficient amount of the test solution through the strip to the situs to separate bound conjugate from unbound conjugate and to bind the unbound conjugate at the situs to produce a signal that is detectible. It is desirable, although not preferred, to position the situs close to the end of the strip which is opposite to the contact portion of the strip. Desirably, the situs should be at least 10 mm, preferably at least 30 mm, from the contact portion of the strip. It may be positioned any greater distance away from the end provided the test solution can pass through the situs by capillary action to capture a sufficient amount of the unbound conjugate. In this way, the situs is "separated" from such end portion. Where several situses are used, the situses can be grouped close together or apart but must not be so close as to compromise resolution of the signal. Consequently, such situses usually should be spaced not less than 1 mm apart, preferably at least 3 mm apart.

Other reagents which are members of the signal producing system can vary widely in concentration depending upon the particular protocol and their role in signal production. Usually the antibody for the analyte will not exceed $10^3$ times the maximum concentration of interest of the analyte when the analyte has multiple binding sites and will not exceed $10^3$ times the maximum concentration of interest when a monovalent analyte is used. Normally, the antibody for the analyte will not be less than about 0.5 times the minimum concentration of interest. The amount of conjugate will usually be equal (in moles) to that of the antibody for the analyte.

In carrying out the assay, the protocol will normally involve combining in an aqueous medium the sample suspected of containing the analyte with the antibody for the analyte and the conjugate to form the aqueous test solution. The sample may be derived from a wide variety of sources, such as physiologic fluids, illustrated by saliva, blood, serum, plasma, urine, ocular lens fluid, spinal fluid, etc., chemical processing streams, food waste water, etc.

The contact portion of the bibulous material, usually, the end opposite the situs, is contacted with the test solution, usually by immersion of the contact portion into the test solution. Wetting of the bibulous material by capillary action usually is allowed to continue at least until the situs is wet. Preferably, at least half the strip is wet with the test solution. When downward syphoning flow is used, usually the entire strip will be wet and excess test solution can be allowed to syphon through the strip.

For the most part, relatively short times are involved for the test solution to traverse the strip. Usually, the traverse of the test solution over the strip will take at least 30 sec and not more than 1 hour, more usually from about 1 min to 30 min. The development of the signal will generally range from 30 sec to 30 min, more usually from about 30 sec. to 5 min.

After the liquid has traversed the strip at least to the situs, the strip or the situs is exposed to the signal producing means. Where chemical agents form part of the signal producing means, this may be accomplished by immersion of the strip into the developer solution or by contacting the contact portion of the strip with the developer solution and allowing the solution to traverse the strip by capillary action at least to the small situs and preferably until the entire strip is wet.

When an enzyme is used as a label, the substrate will normally be in substantial excess in the developer solution, so as not to be rate limiting (greater concentration than Km). The developer solution will usually be appropriately buffered for the enzyme system.

After contacting the strip with the developer solution, the strip is contacted with any remaining members of the signal producing system not present in the developer or test solutions or present on the strip. A sufficient time is allowed to elapse prior to measuring the signal to produce an amount of the signal producing compound required to define the region of the situs in which the analyte is bound. Once the detectable signal has been produced, the presence or absence of the analyte or analytes in the sample is known.

The strip can be coated with a wide variety of materials to provide for enhanced properties. Coatings may include protein coatings, polysaccharide coatings, synthetic polymers, sugars or the like, which are used particularly to enhance the stability of the materials conjugated to the strip. These compounds can also be used for improved binding of the materials, such as antibody binding or the like.

The strip, or the situs, can be activated with reactive functionalities to provide for covalent bonding of the organic materials to be conjugated to the strip such as those described in U.S. Pat. No. 4,168,146.

The amount of first receptor which is bound to the strip at the situs will vary depending upon the amount required to bind a sufficient amount of the unbound conjugate to enable an effective assay. Generally, the amount of first receptor at the situs will be at least 1 $\mu g/cm^2$.

The amount of second receptor which is bound to the strip between the situs and the contact portion should be sufficient to bind substantially all of the bound conjugate. Generally, the amount of second receptor will be at least 1 $\mu g/cm^2$.

The first receptor and the second receptor and, where desired, members of the signal producing system, can be bound to the strip by adsorption, rather than covalent bonding, as long as such binding is non-diffusive. This will involve contacting the bibulous support with a solution containing the materials to be bound to the strip and allowing the strip to dry. In general, this procedure will be useful only where the bibulous support is relatively hydrophobic or has a high surface charge, and subsequent treatment with proteins, detergents, polysaccharides, or other materials capable of blocking non-specific binding sites will be required.

One may also assay a test solution for a plurality of analytes such as drugs or screen for one or more of a plurality of analyte. In this situation the test solution is formed by mixing together in an appropriate liquid medium the sample, a plurality of conjugates each comprising one of the analytes, such as drugs, and a label, and a plurality of antibodies, each specific to one or more of the analytes corresponding to the number of analytes for which one desires to test. If it is only desired to know if any one of the drugs is present such as in a screening assay, the bibulous strip contains a situs with one or more receptors non-diffusively bound to it to provide that binding can occur with each of the conjugates. It is necessary to include on the strip between the situs and the contact portion one or more second receptors capable of binding each of the above antibodies. If it is necessary to know which drugs are present, the strip contains a separate situs for each drug. To each situs is bound a first receptor capable of binding to a different conjugate. Where each of the antibodies is from the same species, antibody for that species immunoglobulin can be employed as the second receptor.

In one embodiment of the invention the first receptor can be non-diffusively bound to particles or beads. The particles or beads can then be applied to the strip at the situs. The nature of the particle or the beads may vary widely, being naturally occurring or synthetic. The materials are commercially available or commercially available materials may be modified. Exemplary of such particles or beads are latex particles made from polystyrene, polyacrylates, polyacrylamide, available as Biogel-p ®, or naturally occurring materials such as polysaccharides, particularly cross-linked polysaccharides, such as agarose, which is available as Sepharose ®, dextran, available as Sephadex ®, microcrystalline cellulose, starch and the like. Other materials include polyacrylamides, polystyrene, polyvinyl alcohol, copolymers of hydroxyethyl methacrylate and methyl methacrylate, silicones, glasses, available as Bioglas ®, diatomaceous earth, silica, and the like. The primary requirement is that the materials do not contribute a signal, usually light absorption, that would cause the signal at the situs to be unrelated to the amount of analyte in the sample.

The particles must be capable of non-diffusivable attachment to the first receptor where the attachment can be achieved by covalent or non-covalent binding. When the first receptor is covalently bound, the particles should be polyfunctional or be capable of being polyfunctionalized. A wide variety of functional groups are available or can be incorporated. Functional groups include carboxylic acids, aldehydes, amines, amides, activated ethylenes such as maleimide, hydroxyls, sulfonic acids, mercaptans, and the like. The manner of linking a wide variety of compounds to the various particles is well known and is amply illustrated in the literature. See, for example, Cautrecases, *J. Biol. Chem.* 245, 3059 (1970).

The length of the linking groups will vary widely depending upon the nature of the compound being linked, the effect of distance between the label and the particle on the label's properties, the potential for cross-linking of the labels, and the like.

The particles should not migrate to any significant degree. The size of the particles can vary but must be of a size to infiltrate the pores of the bibulous material and become imbedded or non-diffusively bound therein. Thus, the particles are generally slightly larger than the minimum size of the pores of the bibulous material and smaller than the maximum pore size. Usually, the size of the particles will range from about 0.1 to 50 microns, more usually from about 0.4 to 10 microns, preferably greater than $0.5\mu$.

Particles having a non-diffusively bound first receptor may be used to non-diffusively bind the first receptor to the strip at the situs with sharply defined edges. Several methods may be employed. Usually a suspension of the particles in a liquid, that frequently is aqueous, will be applied to the strip. Application may be by any standard printing process including the use of electrostatic and laser propelled jets, and printing probe or type face. In addition, particles could be applied by template. The shape of the situs would be defined by a cut pattern through which particles would be absorbed into the bibulous strip. Alternatively, the suspension can be transferred to the strip by inscribing with a pen or microcapillary tube. Where dry particles are used, they may be applied by directing a jet of a suspension of the particles in a gas, usually air, at the desired situs. In each case, particularly when printing techniques are not used, it will frequently be desirable to provide for reduced pressure on the side of the strip opposite to the side used to apply the particles. Pressure reduction is conveniently provided by placing a sheet of the bibulous material on a filter or porous plate that covers a vacuum chamber. The suspension is then applied while air is being drawn through the material. Regardless of the method of application of the particles it is usually preferable to wash the situs free of unbound particles after they have been applied.

The liquid used to suspend the particles will usually be aqueous and must not dissolve the particles or damage or release the bound first receptor. Thickners and surfactants may be added to limit capillary flow and provide sharply defined edges. Thickners may include polyvinyl alcohol, polypyrrolidone, dextran, glycerol, and the like. Surfactants may be ionic, usually anionic, or non-ionic.

In one embodiment of the present invention, the analyte is a monovalent drug. The sample suspected of containing the drug is mixed with a conjugate of an enzyme and the drug and antibody for the drug in an appropriate medium to form the aqueous test solution. The antibody for the drug will bind to the drug and to the conjugate. The bibulous strip will contain antibody for the enzyme at the situs, which will bind to conjugate that does not bind to antibody for the drug. The situs is a band opposite the contact portion of the strip. Antibody specific for the antibody for the drug is non-diffusively bound to the strip between the situs and the contact portion. As a consequence, antibody bound drug and antibody bound conjugate are captured prior to the test solution reaching the situs when the contact portion is contacted with the test solution. The amount of antibody specific for the antibody for the drug is selected to bind all of the antibody bound drug and antibody bound conjugate. When the sample, the conjugate, and the antibody for the drug are mixed together to form the test solution and the drug is present in the sample, a complex between the drug and the antibody for the drug and between the conjugate and antibody for the drug are formed. The more drug in the sample, the less conjugate becomes bound by antibody for the drug. The antibody bound drug and the antibody bound conjugate are captured prior to the test solution reaching the situs. Unbound conjugate moves along the bibulous strip until it reaches the situs to which it becomes bound due to binding with anti-enzyme at the situs. If the drug is not present in the sample, then all the conjugate will be bound by antibody for the drug and captured prior to reaching the situs since this antibody is present in excess quantity. In subsequent development of the test strip, the presence of drug in the sample will be indicated by production of a signal at the situs. The test solution can traverse all or part of the strip by capillary action. If the test solution is allowed to traverse the strip through the situs, the strip can subsequently be immersed in the developer solution.

In a variant of the above-described embodiment, the volume of the test solution may be sufficient to permit it to traverse only a portion of the strip such that the fluid capacity at the dry portion of the strip is at least as great as the fluid capacity of the portion from the contact portion through the situs. The contact portion of the strip is next contacted with the developer solution. The developer solution moves along the strip through the situs by capillarity. In doing so, the developer solution causes the remainder of the test solution to move through the small situs. If analyte is present in the test solution, a signal is generated.

In another variant of the above-described embodiment the conjugate of the analyte and the label is further bound to biotin. The assay is carried out in the same way but the first receptor is anti-biotion such as avidin or antibody for biotin. When analyte is present, some biotinylated conjugate reaches the situs and is bound by the anti-biotin.

As a matter of convenience, the present device can be provided in a kit in packaged combination with predetermined amounts of reagents for use in assaying for an analyte or a plurality of analytes. Where an enzyme is used as the label, the reagents will include enzyme labeled analyte and antibody for the analyte and the developer solution can contain substrate for the enzyme or precursors therefor including any additional substrates, enzymes and cofactors and any reaction partner of the enzymic product required to provide the detectable chromophore or fluorophore. In addition, other additives such as ancillary reagents may be included, for example, stabilizers, buffers, and the like. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay.

EXAMPLES

The invention is demonstrated further by the following illustrative example. Before proceeding with a description of the illustrative example, a number of terms will be defined.

| | |
|---|---|
| IgG: | immunoglobulin G |
| GO: | glucose oxidase |
| HRP: | horseradish peroxidase |
| Anti-MIgG: | antibody for mouse IgG prepared according to standard techniques by immunizing sheep with mouse antibody for IgG and collecting sera. |
| BGG: | bovine gamma globulin |
| BSA: | bovine serum albumin |
| Anti-HRP: | antibody for HRP prepared according to standard techniques. |
| PO4 | mono- and dibasic phosphate, sodium salt |
| Anti-drug: | antibody for a drug prepared according to standard techniques. |
| HRP-drug conjugate | drug conjugated to HRP prepared according to standard N-hydroxy succinimide ester activation techniques |

EXAMPLE 1

Preparation of Solid Phase

Anti-MIgG (2 mg/ml) or anti-HRP (0.75 mg/ml) plus GO (0.1 mg/ml) bulked to 2 mg/ml was placed in 0.1M NaHCO3 at pH 9.5. Carbonyldiimdazole activated paper (prepared in accordance with U.S. Pat. No. 4,330,440 was dipped into the above mixture (either anti-MIgG or anti-HRP) then removed. The paper was incubated for 1 hour on the bottom of a glass plate. Ethanolamine at 0.1M in NaHCO3 at pH 9.5 was added to the paper and incubated overnight. The paper was washed 3 times in (Na+) PO4 pH 7 for 20 minutes each, then in water for 20 minutes. The paper was dried in a tunnel drier for 7 minutes at 70° C.

Anti-MIgG paper was cut into 6 cm wide sections and the anti-HRP/GO paper was cut into 3 cm wide sections. Both papers were placed on a 9 cm piece of plastic coated with adhesive. The papers were placed so that they butted up against each other. Once affixed to the plastic the whole assembly was cut into 9 by 0.45 cm strips.

Short sticks were also made. These were 6 cm long containing 4 cm of anti-MIgG paper and 2 cm of anti-HRP/GO paper.

EXAMPLE 2

Optimization of Anti-drug

Anti-drug was serially diluted 1:2 in 0.1M (NA+)-PO4, 0.2M NaCl pH 7.0 with 2 mg/ml BGG. HRP-drug conjugate was diluted to 200 ng/ml in the same buffer. Anti-drug and conjugate were added together in equal amounts (1 ml total). Anti-MIgG/anti-HRP/GO strips were added to the anti-drug conjugate solution. The end portions of the strips were contacted with the solution, which was allowed to wick (with the anti-IgG portion in solution). When wicking was completed the strip was transferred into developer solution (4-chloro-1-naphthol and glucose) and developed for 5 minutes. Optimum anti-drug concentration was determined by the minimum amount of anti-drug which allowed no color to develop on the top portion of the strip (the situs containing anti-HRP/GO).

EXAMPLE 3

Qualitative Assay

Protocol one: Sample (10 μl) was added to 1 ml of optimized anti-drug solution (0.2% BSA in 0.1M [Na+] PO4). HRP-drug conjugate (10 μl) was added to anti-drug mixture. The solution was vortexed and incubated one minute. The stick was added, wicked and developed as above. A positive result was indicated by color at the situs.

Protocol two: Sample was added to anti-drug solution at twice the concentration of optimized anti-drug. Next, an equal amount of HRP-drug conjugate solution was added to the anti-drug solution (total volume 0.5 ml). The end portion of the stick was contacted with the solution which was allowed to wick up the stick. The stick was developed as above.

Protocol three: A single reagent was made containing both anti-drug and drug conjugate. Sample was added to this and the assay was performed as above.

EXAMPLE 4

Qualitative Assay for Theophylline and Phenobarbitol

| Protocol one was followed. | |
|---|---|
| Anti-drug: | anti-theophylline, anti-phenobarbital |
| HRP-drug conjugate: | HRP-theophylline, HRP-phenobarbital |
| Theophylline concentration: | 0,25,400 ng/1.02 ml assay solution |
| Phenobarbital concentration: | 0,50,800 ng/1.02 ml assay solution |

Each of the above assay solutions were tested. Color bands at the situs developed for those solutions containing theophylline or phenobarbital whereas no color was observed for those solutions not containing drug.

EXAMPLE 5

Qualitative Assay for Tetrahydrocannabinol (THC)

| Protocol two was followed: | |
| --- | --- |
| Anti-drug: | anti-THC |
| HRP-drug conjugate: | HRP-THC |
| THC concentration: | 0,1,10,100,1000 ng/1.01 ml assay solution |

Each of the above assay solutions were tested. Color bands at the situs were observed for those solutions containing THC at a concentration of 10 ng/1.01 ml and above. The 0 and 1 ng/1.01 ml solutions gave no color at the situs.

EXAMPLE 6

Qualitative Assay for Theophylline, Phenobarbitol and Quinidine

| Protocol two was followed. | |
| --- | --- |
| Anti-drug: | anti-theophylline, anti-phenobarbitol, and anti-quinidine |
| HRP-drug conjugate: | HRP-theophylline, HRP-phenobarbitol, and HRP-quinidine |
| Theophylline concentration: | 0,25,400 ng/1.01 ml assay solution |
| Phenobarbitol concentration: | 0,50,800 ng/1.01 ml assay solution |
| Quinidine concentration: | 0,5,80 ng/1.01 ml assay solution |

Each of the above assay solutions were tested. Color bands at the situs were observed for those solutions containing theophylline, phenobarbitol, or quinidine whereas no color was observed for those solutions not containing drug.

EXAMPLE 7

Qualitative Assay for Theophylline

| Protocol three was followed. | |
| --- | --- |
| Anti-drug: | anti-theophylline |
| HRP-drug conjugate: | HRP-theophylline |
| Theophylline concentration | 0,25,50,100,200,400 ng/1.01 ml assay solution |

Each of the above assay solutions were tested. Color bands at the situs were observed for those solutions containing theophylline. No color was observed in the absence of drug.

The present invention provides a number of significant advantages over known methods. A primary advantage of the present invention is that one or more analytes can be determined in a single assay on a single test element. This provides a savings in operator's time and in cost. The test element is completely versatile and can be the same for all assays independent of the drug to be tested. The reagents and devices can be manufactured easily and inexpensively which provides an additional cost savings. The assay result can be determined by reference solely to the assay device and, when the signal produced is a color or fluorescence, the device can be read without the aid of an instrument. Therefore, a built-in control can be provided. A positive result can easily be distinguished over any background produced on the test device as the result of non-specific interactions. Also, the factors producing background signal affect the situs and the remaining area of the test device in substantially the same way.

Another advantage of the present invention is that cumbersome separation techniques are avoided. The assay device is a bibulous strip that is easy to manipulate for separating antibody bound and unbound reagents. The bound reagent is captured prior to the test solution reaching the situs. Another advantage is that assay optimization can be done completely in the solution phase. Thus, optimization of solid phase antibody is avoided. Although the foregoing invention has been described in some detail by way of illustration and example for the purposes of clarity and understanding, it will be obvious that certain changes or modifications may be practiced within the scope of the appended claims.

What is claimed is:

1. A device for determining the presence of an analyte that is capable of binding specifically to an antibody in a test solution comprised of an antibody for said analyte, a conjugate of said analyte and a label, and a sample suspected of containing the analyte, said device comprising
    a piece of bibulous material capable of traversal by said test solution by capillary migration, said bibulous material having a contact portion for contacting said test solution and
    a receptor for said conjugate non-diffusively bound to a situs on said bibulous material separated from said contact portion, the surface area of said situs being less than that of said bibulous material, said bibulous material further containing a second antibody capable of binding said antibody for said analyte, said second antibody being non-diffusively bound to said bibulous material at least at a portion thereof between said situs and said contact portion.

2. The device of claim 1 wherein said bibulous material is paper.

3. The device of claim 1 wherein said receptor is an antibody.

4. The device of claim 1 wherein said analyte is monoepitopic.

5. The device of claim 1 wherein said analyte is a drug.

6. The device of claim 1 wherein said situs is a band transverse to the direction of traversal of said test solution along said bibulous material.

7. The device of claim 1 wherein said label is an enzyme and a second enzyme is bound to said bibulous material at said situs, the enzymes being related in that the product of one enzyme is the substrate for the other.

8. A kit for use in determining the presence of an analyte in a test solution, comprising in a packaged combination—
    (a) an antibody for said analyte
    (b) a conjugate of said analyte and a label
    (c) the device of claim 7.

9. The device of claim 1 for determining the presence of a plurality of analytes in said test solution wherein said test solution comprises a plurality of conjugates each comprising one of said analytes and a label, and a plurality of antibodies each specific to one or more of said analytes, which device further comprises a plurality of situses, non-contiguous with each other and with said contact portion of said bibulous material, each having non-diffusively bound thereto a different receptor capable of binding to a different conjugate.

10. A kit for use in determining the presence of an analyte in a test solution, comprising in a packaged combination—
(a) an antibody for said analyte,
(b) a conjugate of said analyte and a label, and
(c) the device of claim 1.

11. A device for determining the presence of one or more of a plurality of analytes, each capable of binding specifically to an antibody, in a test solution comprised of one or more of a plurality of antibodies each for one of said analytes, one or more of a plurality of conjugates of one of said analytes and a label, and a sample suspected of containing one or more of the analytes, said device comprising—
a piece of bibulous material capable of traversal by said test solution by capillary migration, said bibulous material having a contact portion for contacting said test solution, and
one or more of a plurality of first receptors each for one of said conjugates non-diffusively bound to a situs on said bibulous material separated from said contact portion, the surface area of said situs being less than that of said bibulous material, said bibulous material further containing one or more second receptors capable of binding all of said antibodies, said one or more second receptors being non-diffusively bound to said bibulous material at least between said situs and said contact portion.

12. The device of claim 11 wherein said bibulous material is paper.

13. The device of claim 11 wherein said first receptor is an antibody.

14. The device of claim 11 wherein said second receptor is an antibody.

15. A kit for use in determining the presence of an analyte in a test solution, comprising in a packaged combination—
(a) an antibody for said analyte,
(b) a conjugate of said analyte and a label, and
(c) the device of claim 11.

* * * * *